United States Patent [19]

Schenk

[11] Patent Number: Plant 6,440

[45] Date of Patent: Dec. 6, 1988

[54] LILIUM COMPASS

[75] Inventor: Peter Schenk, Wieringerwerf, Netherlands

[73] Assignee: Bischoff Tulleken Leliecultuur B.V., Wieringerwerf, Netherlands

[21] Appl. No.: 947,440

[22] Filed: Dec. 29, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant, particularly distinguished by its very large flowers unusual color and long persistence, both on the plant and as cut flowers.

It is also characterized by its regular and attractive inflorescence, the greenish/orange color of its buds, the very large flowers, its characteristic tepal spotting and the brilliant orange color of its flowers.

1 Drawing Sheet

BACKGROUND AND GENERAL STATEMENT OF THE INVENTION

My new variety of lily plant is classified botanically as a Lilium hybrid, commercially as an upright Asiatic hybrid Division 1 A in the Horticultural Classification of the Genus Lilium adopted by The Royal Horticultural Society of London.

My new variety of lily plant originated as a seedling selected from a group of seedlings of test crosses at Bischoff Tulleken Leliecultuur B.V., Wieringerwerf, Holland.

The breeding program was initiated in 1977 and the lily plant first flowered in 1980.

The cross was made during a breeding program having as its objective the production of clear gold/orange unspotted or lightly spotted, upright flower cultivars which would perform adequately when forced into flower under glass throughout the year, in addition to meeting the requirements of vigor, disease resistance and rapid natural propagation in field growth.

Cultivars were sought which would be disease resistant, virus tolerant and not overly susceptible to leaf scorch or bud abortion when forced under glass. The cross was made between the seed parent 'Connecticut King' and the pollen plant was an own seedling named R.-1. Both parents are not patented.

My new plant is characterized by rapid and natural propagation under field conditions and by vigorous and healthy growth when forced under glass without leaf scorch and bud abortion.

My new variety of lily plant has been asexually reproduced by me at Bischoff Tulleken Leliecultuur, Wieringerwerf, Holland.

Successive generations produced by bulbscale propagation and natural propagation from bulblets have demonstrated that the novel and distinctive characteristics of my new variety are fixed and hold true under propagation from generation to generation.

THE DRAWINGS

My new variety of lily plant is illustrated in the accompanying photographic drawing which shows the plant, its foliage and its buds in their various stages of development and the open bloom in full color.

DESCRIPTION OF THE NEW VARIETY

The following is a detailed description of my new variety of the Asiatic hybrid lily with nomenclature according to the International Lily Register and with color designations according to The Royal Horticultural Society Colour Chart.

The Plant

Form: Bulbous monocotyledon.

Height: Bulbs 12–16 cm in circumference produce stems: 70–90 cm (28–36") tall when forced into flower under glass; Field grown bulbs produce stems: 60–80 cm (24–32") tall in their second season after scaling.

Growth: Very vigorous and strong.

Foliage: Abundant with about 80–100 leaves per stem.

*Size of leaves.*—8–12 cm (3.2–4.8") long, 1.0–2.0 cm (0.4–0.8") wide.

*Shape of leaves.*—Lanceolate.

*Texture of leaves.*—Leaves entire (not serrated) smooth and glossy on upper sides and lower sides.

*Color of leaves.*—Upperside: medium green. Underside: medium to dark green.

*Ribs and veins of leaves.*—Typical monocotyledonous venation; light green parallel veins.

Stem: Green.

Inflorescence

Well spaced pyramidal raceme with ascending pedicels and no secondary buds. Bulbs which are 12–15 cm (5–6") in circumference produce 5–7 buds. Peduncle and pedicel: Smooth and glossy. Buds are very big and a little bit hairy (pilose). Color of inflorescence: light green with soft organge overlay.

The Buds

Size: 8–10 (3.2–4") long, 2–5 cm (0.8–2") wide.

Form: Lanceolate with obtuse tip; typical of Asiatic hybrid lilies.

Opens slowly: Opens in about one hour in response to (morning) light. Flowers further up the stem open on subsequent days over an interval of 1–2 weeks.

Color of mature buds: Brilliant greenish/orange. RHS CC 26 A.

The Flower

Blooming characteristics: Flowers in midseason, late June and early July in The Netherlands, once, and profusely.

Flower size: Flower diameter is 15–20 cm (6–8″). Inner tepals are 4.0–4.5 cm ($1\frac{1}{2}$–$1\frac{3}{4}$″) wide. Outer tepals are 2.5–3.0 cm ($\frac{3}{4}$–1″) wide.

Shape when flower first opens: Shallow bowl-shape with lightly recurved tepal tips. Tepals recurve more as flower ages.

Tepal arrangement: Typical of the genus Lilium, with 6 entire imbricated tepals.

Color, base of tepals: The basal color is marigold orange CC 24 A RHS changing to a deeper orange RHS CC 26 B as flower ages.

Color, inside tepals: The inside color is RHS CC 24 B changing to RHS CC 26 B when the flower ages.

Color, outer tepals: When fully opened the color is tangerine orange, RHS color code 24 B.

Color, reverse of tepals: The color of the reverse is RHS CC 24 B with orange buff midrib.

Spotting pattern: A few tiny spots, dark brown around the throat of the flower.

Tepal duration: Tepals remain on individual flower for 5–7 days, stem has flowers with tepals adhering for about 3 weeks. Tepals fall as flower ages.

Flower texture: Not affected by hot or wet weather.

The Flower

Pedicel: Pedicel is sturdy and upright ascending at 45° angle.

*Length.*—5–12 cm (2–5″).

*Color.*—Green.

Fragrance: None.

Lasting quality: Flowers remain on plants for about 2–3 weeks. Flowers remain on cut flower stem for about 2 weeks with adequate light.

The Reproductive Organs

Stamens and anthers: Typical of genus Lilium. Six versatile anthers hang (singly) from 6 narrow filaments.

Filaments: 5–6 cm (2″) long and light orange.

Pollen: Reddish brown.

Pistil: 1, typical of genus Lilium. Style is 5–6 cm (2″) long.

Stigma: Small, light brown reddish.

Ovary: Typical of genus Lilium. Superior, single 6 chambered ovary.

The Fruit

Fertile, capsule is oblong with 6 chambers. Color at maturity is medium green to dark green, sometimes overlaid with soft purple. Fades to soft brown when fruit splits open to release seeds.

The Bulbs

Color of the bulbs: White.

Size of the bulbs: Usual commercial size is 12–20 cm (5–8″) in circumference; bulbs can be grown to a larger size if this is desired.

I claim:

1. A new and distinctive variety of Asiatic hybrid lily plant, substantially as herein shown and described characterized by:

its rapid natural propagation under field conditions;
its vigorous and healthy growth without leaf scorch, when forced under glass;
its regular and attractive inflorescence;
the greenish orange color of its buds;
the very big size of the buds;
the very large size of its flowers;
the great width of its tepals,
the typical character of its tepal spotting;
the brilliant orange color of its flowers;
and the long life of its flowers.

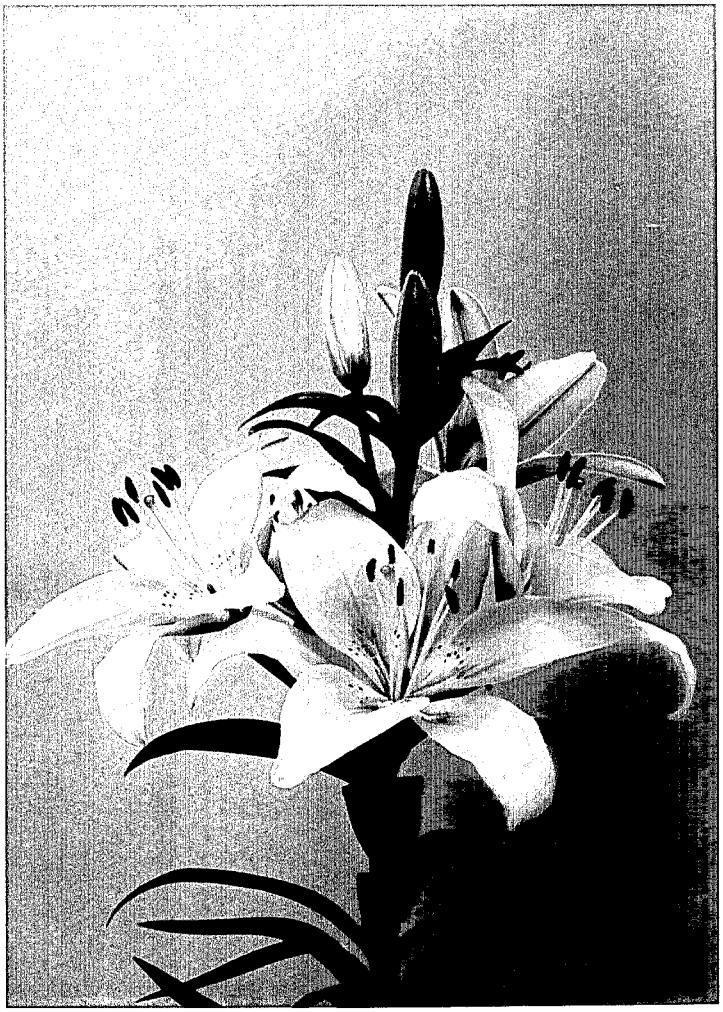

* * * * *